United States Patent
Roscoe et al.

(10) Patent No.: US 9,435,739 B2
(45) Date of Patent: Sep. 6, 2016

(54) METHODS AND COMPOSITIONS TO DETECT A BIOLOGICAL ACTIVITY

(75) Inventors: Stephen B. Roscoe, Woodbury, MN (US); Kurt J. Halverson, Lake Elmo, MN (US); Jesse D. Miller, Hudson, WI (US); Stephanie J. Moeller, Stillwater, MN (US); Jason W. Bjork, Newport, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 232 days.

(21) Appl. No.: 13/883,620

(22) PCT Filed: Oct. 28, 2011

(86) PCT No.: PCT/US2011/058214
§ 371 (c)(1),
(2), (4) Date: May 6, 2013

(87) PCT Pub. No.: WO2012/071131
PCT Pub. Date: May 31, 2012

(65) Prior Publication Data
US 2013/0230876 A1 Sep. 5, 2013

Related U.S. Application Data

(60) Provisional application No. 61/416,858, filed on Nov. 24, 2010.

(51) Int. Cl.
*C12Q 1/44* (2006.01)
*G01N 21/64* (2006.01)
*C12Q 1/04* (2006.01)

(52) U.S. Cl.
CPC ............. *G01N 21/6486* (2013.01); *C12Q 1/04* (2013.01)

(58) Field of Classification Search
CPC .............................. G01N 21/6486; C12Q 1/04
See application file for complete search history.

(56) References Cited

U.S. PATENT DOCUMENTS

| 4,565,783 | A | 1/1986 | Hansen et al. |
| 5,089,413 | A | 2/1992 | Nelson et al. |
| 5,232,838 | A | 8/1993 | Nelson et al. |
| 5,316,906 | A | 5/1994 | Haugland et al. |
| 5,443,986 | A | 8/1995 | Haughland et al. |
| 5,601,998 | A | 2/1997 | Mach et al. |
| 5,605,812 | A * | 2/1997 | Zomer .......................... 435/38 |
| 5,681,712 | A | 10/1997 | Nelson |
| 6,372,895 | B1 * | 4/2002 | Bentsen ............... C07H 17/075 530/300 |
| 6,556,508 | B2 | 4/2003 | Tsao et al. |
| 7,141,387 | B2 | 11/2006 | Ushiyama |
| 2007/0128589 | A1 | 6/2007 | Sanders et al. |

FOREIGN PATENT DOCUMENTS

| EP | 0 000 063 | 12/1978 |
| EP | 0 347 771 | 12/1989 |
| EP | 2 256 103 | 12/2010 |
| GB | 1 547 747 | 6/1979 |
| WO | WO 2004/027084 | 4/2004 |
| WO | WO 2012/012104 | 1/2012 |
| WO | WO 2012/012106 | 1/2012 |

OTHER PUBLICATIONS

Liu X. et al., Fabrication of a microfluidic enzyme reactor utilizing magnetic beads, Electrophoresis, 2009, vol. 30, pp. 2129-2133.*
Chilvers, K.F. et al.; "Synthesis and evaluation of novel fluorogenic substrates for the detection of bacterial β-galactosidase"; Journal of Applied Microbiology; vol. 91; 2001; pp. 1118-1130.
Sernetz, M. et al.; "A New Method for the Evaluation of Reaction Kinetics of Immobilized Enzymes Investigated in Single Enzyme-Sepharose Beads by Microfluorometry"; Analytical Biochemistry; vol. 72, No. 1-2; 1976; pp. 24-37 (XP024830767).
Vargas, F.; "Preparation and Quantification of 3'-Phosphoadenosine 5'-Phosphol[$^{35}$S]sulfate with High Specific Activity"; Analytical Biochemistry; vol. 172; 1988; pp. 82-88.

* cited by examiner

*Primary Examiner* — Satyendra K Singh
(74) *Attorney, Agent, or Firm* — Qiang Han

(57) ABSTRACT

Compositions that comprise water, a first indicator reagent that can be converted by a first biological activity to a first biological derivative, and a plurality of particles are provided. The first indicator reagent can comprise a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores. The particles are capable of receiving and retaining the first biological derivative from an aqueous liquid. The first biological derivative can be indicative of a microorganism. The compositions further can comprise a gelling agent. Methods of using the compositions to detect the presence or absence of a microorganism in a sample are also provided.

3 Claims, 2 Drawing Sheets

METHODS AND COMPOSITIONS TO DETECT A BIOLOGICAL ACTIVITY

CROSS REFERENCE TO RELATED APPLICATIONS

This application is a national stage filing under 35 U.S.C. 371 of PCT/US2011/058214, filed Oct. 28, 2011, which claims the benefit of U.S. Provisional Patent Application No. 61/416,858, filed Nov. 24, 2010, which is incorporated hereby by reference in its entirety.

BACKGROUND

Methods for detecting a target microorganism in a sample frequently include the use of an indicator reagent that is acted upon by the target microorganism to form a detectable product. For example, the biological activity may be detected by a catalytic activity associated with a cell, such as a pathogenic microorganism, a biological indicator organism, or a cancer cell.

The detection of a particular biological activity in a sample can be indicative of particular microorganisms in the sample. Bacterial spores, for example, include biological activities (e.g., enzyme activities such as α-glucopyranosidase or β-glucopyranosidase) that may be used in methods (e.g., including rapid methods) detect the presence of viable spores in a sample. Destruction of one of these or other biological activities can be used to verify and/or validate the efficacy of a sterilization process.

SUMMARY OF THE INVENTION

The present disclosure relates generally to compositions, articles and methods to detect the presence or absence of a biological activity in a sample. In some embodiments, a presence or absence of the biological activity can indicate the presence or absence of a microorganism. The inventive methods include providing fluid communication between a sample, a first indicator reagent that can be converted by a first biological activity to a first biological derivative, and a plurality of particles that are capable of receiving and retaining the first biological derivative from an aqueous liquid. Advantageously, the first biological derivative can partition from the aqueous liquid onto and/or into the particles, thereby concentrating the first biological derivative into a relatively small area or volume. Partitioning the first biological derivative onto and/or into the particles can make the first biological derivative more easily detectable than it might otherwise be in the aqueous liquid. Furthermore, the particles can substantially restrict the diffusion of the first biological derivative in a hydrogel, thus permitting the detection of a plurality of separate biological activities, microorganisms, or microcolonies present in a hydrogel.

In one aspect, the present disclosure provides a method of detecting a biological activity. The method can comprise providing a sample that may comprise a first biological activity, a first indicator reagent that can be converted by a first biological activity to a first biological derivative, and a plurality of particles, each particle comprising an organic polymer that receives and retains the first biological derivative. The first indicator reagent can comprise a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores. The method further can comprise forming an aqueous dispersion comprising the first indicator reagent and the plurality of particles; bringing the sample into fluid communication with the aqueous dispersion; and detecting a presence or absence of the first biological derivative, wherein the first biological derivative is retained by a particle.

In any of the above embodiments of the method, detecting the presence or absence of the biological derivative can comprise detecting fluorescent first biological derivative or a colored biological derivative. In any of the above embodiments, the method further can comprise providing a gelling agent, wherein forming the aqueous dispersion comprises forming a hydrogel, wherein at least a portion of the plurality of particles is dispersed in the hydrogel. In any of the above embodiments of the method, providing a gelling agent can comprise providing a cold-water-soluble gelling agent. In some embodiments, the cold water-soluble gelling agent can be selected from the group consisting of hydroxyethyl cellulose, carboxymethyl cellulose, poly-acrylamide, locust bean gum, guar gum, xanthan gum and algin, glycol modified polysaccharides, and starch-graft-poly(sodium acrylate-co-acrylamides).

In some embodiments, the method further can comprise providing a second indicator reagent that can be converted by a second biological activity to a second biological derivative, bringing the second indicator reagent into fluid communication with the hydrogel, and detecting a presence or absence of the second biological derivative. When the second indicator reagent comprises a fluorogenic enzyme substrate, the second indicator reagent can have a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores.

In any of the above embodiments, the method further can comprise providing a second indicator reagent that can be converted by a second biological activity to a second biological derivative and detecting a presence or absence of the second biological derivative. When the second indicator reagent comprises a fluorogenic enzyme substrate, the second indicator reagent can have a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores. Forming the aqueous dispersion can comprise forming an aqueous dispersion comprising the second indicator reagent.

In any of the above embodiments of the method, bringing the sample into fluidic contact with the aqueous dispersion can comprise forming the aqueous dispersion comprising the sample, the first indicator reagent, and the plurality of particles.

In any of the above embodiments of the method, after bringing the sample into fluid communication with the aqueous dispersion, the method further can comprise separating a portion of the plurality of particles from or within the aqueous dispersion. In some embodiments, separating the portion comprises separating the portion by sedimentation, centrifugation, flocculation, or filtration.

In another aspect, the present disclosure provides a method of detecting a biological activity. The method can comprise providing a sample that may comprise a first biological activity; a first indicator reagent that can be converted by a first biological activity to a first biological derivative; a plurality of particles, each particle comprising an organic polymer that receives and retains the first biological derivative; and a gelling agent. The first indicator reagent can comprise a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores. The method further can comprise forming a hydrogel comprising the first indicator reagent and the gelling agent, distributing the particles on at least a portion of a major surface of the hydrogel, bringing the sample into fluid communication with a portion of the hydrogel, and detecting a presence or absence of the first biological derivative, wherein the first biological derivative is retained by a particle. In some embodiments, detecting the presence or absence of the first biological derivative can comprise detecting a fluorescent first biological derivative or a colored first biological derivative. In some embodiments, providing the gelling agent can comprise providing a cold water-soluble gelling agent. In some embodiments, the cold-water-soluble gelling agent can be selected from the group consisting of hydroxyethyl cellulose, carboxymethyl cellulose, poly-acrylamide, locust bean gum, guar gum, xanthan gum and algin, glycol modified polysaccharides, and starch-graft-poly(sodium acrylate-co-acrylamides). In some embodiments, the method further can comprise providing a second indicator reagent that can be converted by a second biological activity to a second biological derivative, bringing the second indicator into fluid communication with the hydrogel, and detecting a presence or absence of the second biological derivative. When the second indicator reagent comprises a fluorogenic enzyme substrate, the second indicator reagent can have a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores. In some embodiments, distributing the particles on at least a portion of a major surface of the hydrogel further can comprise bringing the second indicator reagent into fluid communication with the hydrogel. In some embodiments, bringing the sample into fluid communication with the at least a portion of a major surface of the hydrogel further can comprise bringing the second indicator reagent into fluid communication with the hydrogel. In some embodiments, forming the hydrogel further can comprise forming the hydrogel comprising the second indicator reagent. In some embodiments, detecting a presence or absence of the first biological derivative can comprise detecting discrete fluorescent zones. In some embodiments, detecting discrete fluorescent zones further comprises counting a quantity of discrete fluorescent zones. In some embodiments, detecting a presence or absence of the first biological derivative can comprise detecting discrete colored zones. In some embodiments, detecting discrete fluorescent zones further comprises counting a quantity of discrete colored zones.

In yet another aspect, the present disclosure provides a composition. The composition can comprise water; a first indicator reagent that can be converted by a first biological activity to a first biological derivative; and a plurality of particles, wherein the particles capable of receiving and retaining the first biological derivative from an aqueous liquid. The first indicator reagent can comprise a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores. In some embodiments, the composition further can comprise a nutrient to facilitate the growth of a microorganism. In any of the above embodiments, the composition further can comprise a gelling agent. In some embodiments, the gelling agent can react with the water to form a hydrogel. In some embodiments, the gelling agent can comprise a cold-water-soluble gelling agent. In some embodiments, the cold-water-soluble gelling agent can be selected from the group consisting of hydroxyethyl cellulose, carboxymethyl cellulose, poly-acrylamide, locust bean gum, guar gum, xanthan gum and algin, glycol modified polysaccharides, and starch-graft-poly(sodium acrylate-co-acrylamides). In some embodiments, at least a portion of the plurality of particles can be dispersed in the hydrogel. In some embodiments, at least a portion of the plurality of particles can be disposed on a major surface of the hydrogel. In any of the above embodiments, the composition further can comprise a surfactant. In any embodiment of the composition, the particles can comprise an organic polymer selected from the group consisting of acrylate polymers, polystyrene polymers, cellulosic polymers, dextran polymers, combinations of any of the foregoing and derivatives of any of the foregoing.

In yet another aspect, the present disclosure provides an article. The article can comprise a body member comprising a self-supporting, waterproof substrate having a first major surface and a second major surface; and a coating adhered to a least a portion of the first major surface, wherein the coating comprises a gelling agent and a plurality of particles. The particles can receive and retain from a hydrogel a first biological derivative of a first indicator reagent. In some embodiments, the gelling agent can comprise a dry, cold-water-soluble gelling agent. In some embodiments, the gelling agent can be selected from the group consisting of hydroxyethyl cellulose, carboxymethyl cellulose, poly-acrylamide, locust bean gum, guar gum, xanthan gum and algin, glycol modified polysaccharides, and starch-graft-poly(sodium acrylate-co-acrylamides). In any of the above embodiments of the article, the first biological derivative can be a fluorescent compound derived from a fluorogenic enzyme substrate. In any of the above embodiments, the article can further comprise the first indicator reagent. In any of the above embodiments, the first indicator reagent can comprise a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores In any of the above embodiments, the article further can comprise an adhesive layer disposed between the coating and the first major surface, wherein the adhesive layer is disposed between and adhesively coupled to the first major surface and the coating. In any of the above embodiments of the article, the coating further can comprise a nutrient. In any of the above embodiments of the article, the coating or the adhesive layer can comprise a second indicator reagent. In any of the above embodiments of the article, the coating or the adhesive layer further comprises a selective agent. In any of the above embodiments of the article, the particles can comprise an organic polymer selected from the group consisting of acrylate polymers, polystyrene polymers, cellulosic polymers, dextran polymers, combinations of any of the foregoing and derivatives of any of the foregoing. In any of the above embodiments of the article, the coating further comprises a surfactant.

In any of the above embodiments, the particles can be about 0.01 µm to about 1000 µm in diameter.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

"Biological activity", as used herein, refers to any specific catalytic process or groups of processes associated with a biological cell. Nonlimiting examples of biological activities include catabolic enzyme activities, anabolic enzyme activities, coupled reactions (e.g., a metabolic pathway), biomolecule-mediated redox reactions, and bioluminescent reactions.

"Biological derivative", as used herein, refers to any product of a biological activity. This includes, for example, products of enzyme reactions and biological electron transport systems.

"Biological cells", as used herein refer to both unicellular organisms (e.g., bacteria, yeast, filamentous fungi, protozoa, algae), or derivatives thereof, and cells from multicellular organisms (e.g., various types of cells originating from a plant, an animal, or a multicellular fungus), or derivatives thereof. Derivatives of biological cells include dormant states (e.g., spores), genetically-engineered variants, polyploid cells, and hybrid cells (e.g. hybridomas). Biological cells include cells found in natural environments as well as cells that are cultured in vitro.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Other features and aspects of the present disclosure will become apparent by consideration of the detailed description and accompanying drawings.

DETAILED DESCRIPTION

The present disclosure relates to compositions, articles, and rapid methods to detecting a microorganism in a sample. The inventive compositions and articles comprise a plurality of particles that are configured to receive and retain a fluorescent product of a biological activity. Accordingly, the fluorescent molecule can be partitioned (e.g., concentrated) out of an aqueous medium onto and/or into the particles. Advantageously, partitioning the fluorescent molecule onto or into the particle provides a higher local concentration of the fluorescent molecule in the particle than in the surrounding aqueous medium. This concentrating effect can provide a significantly concentrated fluorescent signal, which can be easier to detect over background fluorescence.

Figure 1:
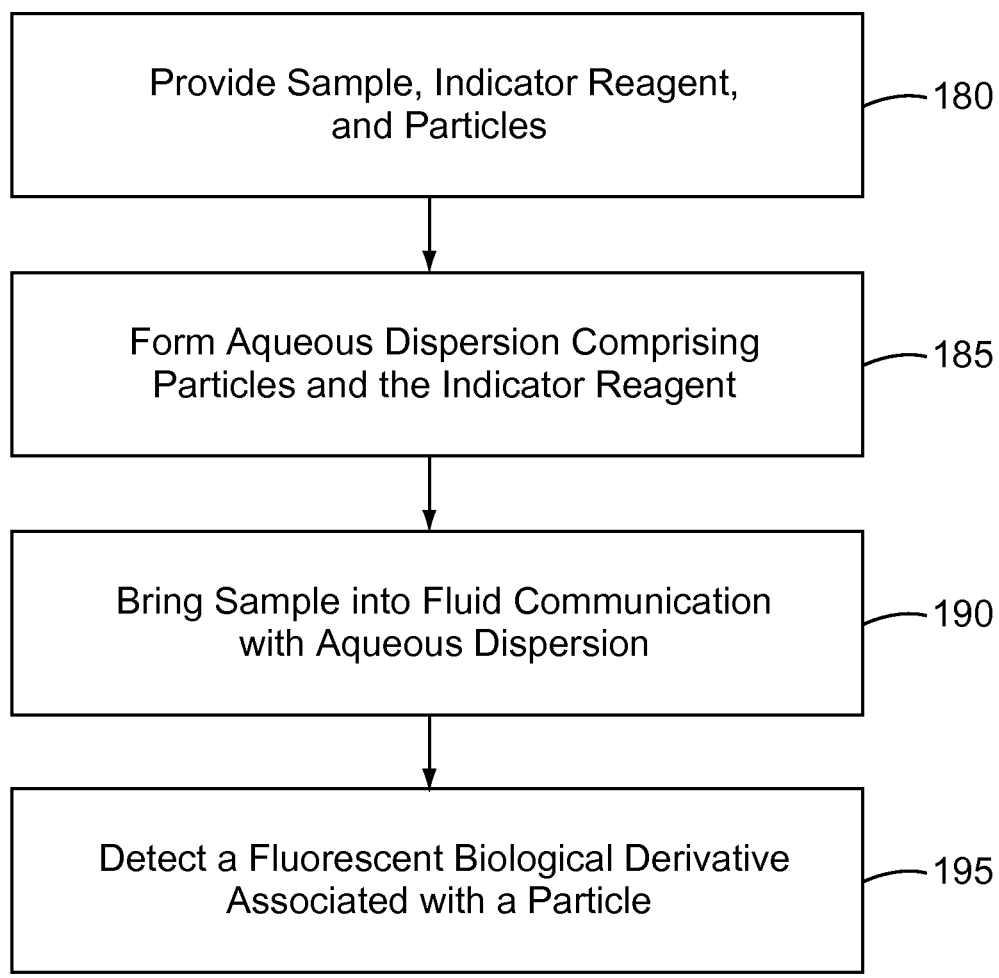
FIG. 1 is a block diagram of one embodiment of a method to detect a biological activity, according to the present disclosure.

In one aspect, the present disclosure provides a method to detect a microorganism in a sample. FIG. 1 shows a block diagram of one embodiment of a method according to the present disclosure. The method comprises the step 180 of providing a sample, a first indicator reagent, and a plurality of particles. The sample can be any suitable sample described herein. The first indicator reagent can be converted by a biological activity to a first biological derivative. The particles can comprise an organic polymer that receives and retains the first biological derivative. The method further comprises the step 185 of forming an aqueous dispersion comprising the first indicator reagent and the plurality of particles, the step 190 of bringing the sample into fluid communication with the aqueous dispersion, and the step 195 of detecting a presence or absence of the first biological derivative retained by a particle.

The inventive method relates to the detection of a biological activity in a sample. The sample can be any sample that includes a biological activity as defined herein. Nonlimiting examples of suitable samples include suspensions or cultures of cells (e.g., mammalian cells, insect cells, yeast cells, filamentous fungi, bacterial cells), environmental samples (e.g., surface swabs), food (e.g., raw materials, in-process samples, and finished-product samples), beverages, clinical samples (e.g., blood, urine, sputum, tissue, mucous, feces, wound exudate, pus), and water (e.g., surface water, potable water, process water).

Microorganisms (e.g., bacteria, fungi, viruses) are a source of biological activity and can be analyzed in a test sample that may be derived from any source, such as a physiological fluid, e.g., blood, saliva, ocular lens fluid, synovial fluid, cerebral spinal fluid, pus, sweat, exudate, urine, mucus, lactation milk, or the like. Further, the test sample may be derived from a body site, e.g., wound, skin, nares, scalp, nails, etc.

Samples of particular interest include mucus-containing samples, such as nasal samples (from, e.g., anterial nares, nasopharyngeal cavity, nasal cavities, anterior nasal vestibule, etc.), as well as samples from the outer ear, middle ear, mouth, rectum, vagina, or other similar tissue. Examples of specific musosal tissues include buccal, gingival, nasal, ocular, tracheal, bronchial, gastrointestinal, rectal, urethral, ureteral, vaginal, cervical, and uterine mucosal membranes.

Besides physiological fluids, other test samples may include other liquids as well as solid(s) dissolved in a liquid medium. Samples of interest may include process streams, water, soil, plants or other vegetation, air, surfaces (e.g., contaminated surfaces), and the like. Samples can also include cultured cells. Samples can also include samples on or in a device comprising cells, spores, or enzymes (e.g., a biological indicator device).

Solid samples may be disintegrated (e.g., by blending, sonication, homogenization) and may be suspended in a liquid (e.g., water, buffer, broth). In some embodiments, a sample-collection device (e.g., a swab, a sponge) containing sample material may be used in the method. Alternatively, the sample material may be eluted (e.g., rinsed, scraped, expressed) from the sample-collection device before using the sample material in the method. In some embodiments, liquid or solid samples may be diluted in a liquid (e.g., water, buffer, broth).

Suitable samples also liquid and/or solid samples that have been exposed to a sterilant. Nonlimiting examples of these samples include spore suspensions, spore strips, and coupons of various materials onto which a suspension of spores or vegetative microbial cells have been applied.

Suitable samples also include cell-suspension media (e.g., culture broth, semi-solid cell culture media, and tissue culture media, filtrate) that contain cells or previously contained cells. Suitable samples also include cell lysates. Cell lysates may be produced by chemical means (e.g., detergents, enzymes), mechanical means (sonic vibration, homogenization, French Press), or by other cell lytic means known in the art.

The sample may comprise a first microorganism. The first microorganism may be a target microorganism than is indicative of contamination (e.g., fecal contamination), infection (e.g., infection with a pathogenic microorganism), or the failure of a sterilization process (e.g., a biological sterilization indicator).

Microorganisms of particular interest include prokaryotic and eukaryotic organisms, particularly Gram positive bacteria, Gram negative bacteria, fungi, protozoa, mycoplasma, yeast, viruses, and even lipid-enveloped viruses. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis, Streptococcus pneumoniae, S. agalactiae, S. pyogenes, Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracia, Pseudomonas aeruginosa, Escherichia coli, Aspergillus niger, A. fumigatus, A. clavatus, Fusarium solani, F. oxysporum, F. chlamydosporum, Listeria monocytogenes, Listeria ivanovii, Vibrio cholera, V. parahemolyticus, Salmonella cholerasuis, S. typhi, S. typhimurium, Candida albicans, C. glabrata, C. krusei, Enterobacter sakazakii, E. coli* O157 and multiple drug resistant Gram negative rods (MDR).

Gram positive and Gram negative bacteria are of particular interest. Of even more interest are Gram positive bacteria, such as *Staphylococcus aureus*. Also, of particular interest are antibiotic resistant microbes including MRSA, VRSA, VISA, VRE, and MDR.

Methods according to the present disclosure include the use of a first indicator reagent. The first indicator reagent can be any suitable indicator reagent described herein. The first indicator reagent can be converted by a biological activity to a first biological derivative. In some embodiments, the first indicator reagent can be an enzyme substrate that is converted by a biological activity (e.g., enzyme activity) to the first biological derivative. Non-limiting examples of suitable biological activities include glycosidase enzymes, esterase enzymes, phosphatase enzymes, sulfatase enzymes, protease enzymes, amidase enzymes, and the like.

In some embodiments, the first indicator reagent comprises a fluorogenic indicator reagent (e.g., a fluorogenic enzyme substrate). It is understood that the fluorogenic indicator reagents are in themselves either nonfluorescent or fluorescent in a distinctly different way, e.g., either by intensity or emission spectrum, than the corresponding biological derivative. Fluorogenic indicator reagents comprise a fluorescent component (fluorophore) with a characteristic fluorescent emission spectrum. In some embodiments, the fluorogenic indicator reagent can be a fluorogenic enzyme substrate. Nonlimiting examples of fluorophores that can be used in first indicator reagents according to the present disclosure include umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores. A "derivative" of any one of the above-mentioned fluorophores, as used herein, refers to a fluorescent molecule comprising the conjugated ring structure of the fluorophore. Exemplary derivatives include, for example, fluorophores in which one or more hydrogen atoms in the original fluorophore are substituted with a functional group such as halogen, alkane, acid, amine, hydroxyl, nitro, sulfate, or the like; provided the substitution does not substantially eliminate the capability of the fluorophore to fluoresce and/or substantially prevent a biological activity from reacting with an indicator reagent comprising the fluorophore derivative. Fluorophores can be coupled to a variety of glycosides, amides, peptides, phosphate, sulfate, or fatty acids, for example to produce a fluorogenic derivative that can be used as a first indicator reagent as described herein.

The prior art includes a number of fluorogenic compounds (e.g., fluorogenic enzyme substrates) of diverse origin which are known, commercially available, have been used in enzymological procedures, and are suitable for use as the first indicator reagent according to the present disclosure. Useful fluorogenic enzyme substrates include water-soluble salts of fluorogenic enzyme substrates.

Among the fluorogenic enzyme substrates are a variety of fluorogenic 4-methylumbelliferyl compounds (hydrolysable to 4-methylumbelliferone); fluorogenic derivatives of 7-amido-4-methyl-coumarin, e.g. as disclosed in GB Patent No. 1,547,747 and European Patent No. 0,000,063, each of which is incorporated herein by reference in its entirety; fluorogenic diacetylfluorescein compounds; and fluorescamine.

Useful fluorogenic 4-methylumbelliferyl compounds include, for example: 4-methylumbelliferyl-2-acetamido-4,6-O-benzylidene-2-deoxy-β-D-glucopyranoside; 4-methylumbelliferyl acetate; 4-methylumbelliferyl-N-acetyl-β-D-galactosaminide; 4-methylumbelliferyl-N-acetyl-α-D-glucosaminide; 4-methylumbelliferyl-N-acetyl-β-D-glucosaminide; 2'-(4-methylumbelliferyl)-α-D-N-acetyl neuraminic acid; 4-methylumbelliferyl α-L-arabinofuranoside; 4-methylumbelliferyl α-L-arabinoside; 4-methylumbelliferyl butyrate; 4-methylumbelliferyl β-D-cellobioside; methylumbelliferyl β-D-N, N'diacetyl chitobioside; 4-methylumbelliferyl elaidate; 4-methylumbelliferyl β-D-fucoside; 4-methylumbelliferyl α-L-fucoside; 4-methylumbelliferyl β-L-fucoside; 4-methylumbelliferyl α-D-galactoside; 4-methylumbelliferyl β-D-galactoside; 4-methylumbelliferyl α-D-glucoside; 4-methylumbelliferyl β-D-glucoside; 4-methylumbelliferyl β-D-glucuronide; 4-methylumbelliferyl p-guanidinobenzoate; 4-methylumbelliferyl heptanoate; 4-methylumbelliferyl α-D-mannopyranoside; 4-methylumbelliferyl β-D-mannopyranoside; 4-methylumbelliferyl oleate; 4-methylumbelliferyl palmitate; 4-methylumbelliferyl phosphate; 4-methylumbelliferyl propionate; 4-methylumbelliferyl stearate; 4-methylumbelliferyl sulfate; 4-methylumbelliferyl β-D-N,N',N"-triacetylchitotriose; 4-methylumbelliferyl 2,3,5-tri-o-benzoyl-α-L-arabinofuranoside; 4-methylumbelliferyl-p-trimethylammonium cinnamate chloride; and 4-methylumbelliferyl β-D-xyloside.

Useful fluorogenic 7-amido-4-methylcoumarin compounds include, for example: L-alanine-7-amido-4-methylcoumarin; L-proline 7-amido-4-methylcoumarin; L-tyrosine-7-amido-4-methylcoumarin; L-leucine-7-amido-4-methylcoumarin; L-phenylalanine-7-amido-4-methylcoumarin; and 7-glutarylphenylalanine-7-amido-4-methylcoumarin.

Useful fluorogenic β-naphthylamine compounds include, for example, Ala-Ala-2-naphthylamide, Ala-Arg-2-naphthylamide, Glu-His-2-naphthylamide, Gly-Arg-2-naphthylamide, Gly-Arg-4-methoxy-2-naphthylamide, Gly-Phe-2-naphthylamide, His-Ser-2-naphthylamide, Phe-Arg-2-naphthylamide, Pro-Arg-2-naphthylamide, α-Asp-Arg-2-naphthylamide, and Gly-Trp-2-naphthylamide.

Useful fluorogenic β-naphthol compounds include, for example, 2-naphthyl acetate, 2-naphthyl-α-D-glucopyranoside, 2-naphthyl phosphate, 2-naphthyl-β-D-glucopyranoside, and 2-naphthyl-α-L-fucopyranoside.

Useful fluorogenic peptide compounds comprising 7-amido-4-methylcoumarin include, for example: N-t-BOC-Ile-Glu-Gly-Arg 7-amido-4-methylcoumarin; N-t-BOC-Leu-Ser-Thr-Arg 7-amido-4-methylcoumarin; N-CBZ-Phe-Arg 7-amido-4-methyl-coumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Useful fluorogenic fluorescein compounds include, for example, fluorescein diacetate, fluorescein mono-(β-D-galactopyranoside), fluorescein di-β-D-galactopyranoside), fluorescein di-β-D-glucopyranoside), fluorescein di-β-D-glucuronide), fluorescein dilaurate, fluorescein diphosphate, and derivatives of any of the foregoing fluorescein compounds.

Useful fluorogenic resorufin compounds include, for example, resorufin-β-D-galactopyranoside, resorufin-β-D-glucuronic acid, resorufin-α-D-mannopyranoside, resorufin ethyl ether, resorufin methyl ether, resorufin benzyl ether, resorufin phosphate and resorufin acetate.

Useful fluorogenic rhodamine compounds include, for example, bis-(aspartic acid amido)rhodamine 110, bis-(CBZ-arginine amido)rhodamine 110, bis-(p-tosyl-L-glycyl-L-prolyl-L-arginine amido)rhodamine 110, bis-(CBZ-L-isoleucyl-L-prolyl-L-arginine amido)rhodamine 110 dihydrochloride, bis-(CBZ-L-arginine amido)rhodamine 110 dihydrochloride, bis-(CBZ-L-alanyl-L-alanyl-L-alanyl-L-alanine amido) rhodamine 110, bis-(N-CBZ-L-aspartyl-L-glutamyl-L-valyl-L-aspartic acid amido) rhodamine 110, bis-(N-CBZ-L-isoleucyl-L-glutamyl-L-threonyl-L-aspartic acid amido)rhodamine 110.

Where the biological activity to be detected is alpha-D-glucosidase, chymotrypsin, or fatty acid esterase, e.g., from *Geobacillus stearothermophilus*, suitable fluorogenic enzyme substrates are 4-methylumbelliferyl-alpha-D-glucoside, 7-glutarylphenylalanine-7-amido-4-methylcoumarin, or 4-methylumbelliferyl heptanoate, respectively. Where the biological activity to be detected is alpha-L-arabinofuranosidase, e.g., derived from *Bacillus subtilis*, a suitable fluorogenic enzyme substrate is 4-methylumbelliferyl-alpha-L-arabinofuranoside. Where the biological activity to be detected is beta-D-glucosidase, e.g., derived from *Bacillus subtilis*, a suitable fluorogenic enzyme substrate is 4-methylumbelliferyl-beta-D glucoside.

Other compounds suitable as first indicator reagents include chromogenic compounds that can be acted upon (e.g., hydrolyzed, oxidized, or reduced) to produce a water-soluble derivative chromophore. It is understood that the chromogenic compounds are in themselves either non-colored or colored in a distinctly different way, e.g., either by color or intensity, than the corresponding first biological derivative. Appropriate wavelengths of detection, in manners well known to users of colorimetric instrumentation are used to separate the colored signal developed by the first biological derivative from any other color that may be present.

A number of chromogenic substrates have been used in enzymological procedures. Among the useful chromogenic substrates are nitrophenyl derivatives and phenolphtalein compounds.

Useful nitrophenyl compounds include p-nitrophenol and o-nitrophenol derivatives. Particularly useful p-nitrophenols include diethyl-p-nitrophenyl phosphate; di-p-nitrophenyl phosphate; p-nitrophenyl-2-acetamido-2-deoxy-3-O-β-galactopyranosyl-β-glucopyranoside; p-nitrophenyl-2-acetamido-2-deoxy-β-glucopyranoside; p-nitrophenyl acetate; p-nitrophenyl-N-acetyl-β-D-glucosaminide; p-nitrophenyl-β-D-N—N'-diacetylchitobioside; p-nitrophenyl-α-glucopyranoside; p-nitrophenyl-α-maltoside; p-nitrophenyl-β-maltoside; p-nitrophenyl-α-mannopyranoside; p-nitrophenyl-β-mannopyranoside; p-nitrophenyl myristate; p-nitrophenyl palmitate; p-nitrophenyl phosphate; bis(p-nitrophenyl)phosphate; p-nitrophenyl-β-glucopyranoside; p-nitrophenyl-β-glucuronide; α-p-nitrophenylglycerine; p-nitrophenyl-α-rhamnopyranoside; nitrophenyl thymidine monophosphate; p-nitrophenyl stearate; p-nitrophenyl sulfate; p-nitrophenyl sulfate; p-nitrophenyl-2,3,4,6-tetra-O-acetyl-β-glucosaminide; p-nitrophenyl thymidine monophosphate; p-nitrophenyl-2,3,4-tri-O-acetyl-β-glucuronic acid methyl ester; and p-nitrophenyl valerate.

Particularly useful chromogenic o-nitrophenol indicators include o-nitrophenyl acetate, o-nitrophenyl-b-glucoside, and o-nitrophenyl-β-D-glucopyranoside. Other particularly useful chromogenic nitrophenyl compounds include nitrophenyl-β-fucopyranoside, nitrophenyl-α-galactopyranoside, nitrophenyl-β-galactopyranoside, nitrophenyl butyrate, nitrophenyl caprate, nitrophenyl caproate, nitrophenyl caprylate, nitrophenyl laurate, and nitrophenyl propionate.

Useful chromogenic phenolphtalein-containing indicators include: phenolthalein dibutyrate; phenolphthalein diphosphate; phenolphthalein disulfate; phenolphthalein glucuronic acid; phenolphthalein mono-β-glucosiduronic acid; phenolphthalein mono-β-glucuronic acid; and phenolphthalein monophosphate.

All of the above-described chromogenic indicator reagents will react directly with an appropriate biological activity (e.g., enzyme) to produce a chromophore.

Additional chromogenic enzyme substrates containing 1-naphthyl, 2-naphthyl and Naphthol-ASBI compounds are usefully employed if the product of the enzyme reaction is further reacted with a chromogenic reagent, such as diazotized dyes, e.g., I-diazo-4-benzoylamino-2,5-diethoxybenzene, (commercially available as "Fast Blue BB Salt" from Sigma Chemical), 1-diazo-4-benzoylamino-2, 5-diethoxybenzene, p-diazo-2,5-diethoxy N-benzoyalanine, 4-chloro-2-methylbenzene diazonium chloride, and o-aminoazotoluene diazonium salt, to produce a chromophor.

Particularly useful chromogenic 1-napthyl compounds include 1-naphthyl-N-acetyl-β-D-glucosaminide Particularly useful chromogenic 2-naphthyl compounds include 2-naphthyl-phosphate; 2-naphthyl-butyrate; 2-naphthyl caprylate; 2-naphthyl-myristate; L-leucyl-2-naphthylamide; L-valyl-2-naphthylamide; L-cystyl-2-naphthylamide; N-benzoyl-DL-arginine-2-naphthylamide; N-glutaryl-phenylalanine-2-naphthyl-amine; 2-naphthyl-phosphate; 6-Br-2-naphthyl-α-D-galactopyranoside; 2-naphthyl-β-D-galactopyranoside; 2-naphthyl-2-D-glucopyranoside; 6-bromo-2-naphthol-β-D-glucopyranoside; 6-bromo-2-naphthyl-2-D-mannopyranoside; and 2-naphthyl-α-L-fucopyranoside.

Particularly useful chromogenic naphthol-ABI compounds include naphthol-ASBI-phosphate; and naphthol-ASBI-β-D-glucuronide.

In some embodiments where the biological activity to be detected is alpha-D-gulucosidase, e.g., from *Geobacillus stearothermophilus*, the chromogenic enzyme substrate is preferably p-nitrophenyl-a-glucopyranoside. In some embodiments where the biological activity to be detected is alpha-L-arabinofuranosidase, e.g., derived from *Bacillus subtilis*, the preferred chromogenic enzyme substrate is p-nitrophenyl-alpha-L-arabinofuranoside. In some embodiments where the biological activity to be detected is beta-D-glucosidase, e.g., derived from *Bacillus subtilis*, a preferred chromogenic enzyme substrate is p-nitrophenyl-β-D-glucopyranoside.

In order to carry out the method of the present invention in detecting a biological activity comprising an enzyme, the operator should be knowledgeable concerning the enzyme activity to be detected and the enzyme substrates that will react with the enzyme so as to produce a product which can be detected either by its fluorescence, color, etc. (see M. Roth, Methods of Biochemical Analysis, Vol. 7, D. Glock, Ed., Interscience Publishers, New York, N.Y., 1969, which is incorporated herein by reference in its entirety). The appropriate enzyme substrate to be utilized will depend upon the biological activity to be detected.

Methods according to the present disclosure include the use of a plurality of particles that comprise an organic polymer material. In some embodiments, the particles are water-dispersible particles, the organic polymer material having functional groups that are relatively hydrophilic. In some embodiments, a surfactant can be added to the particles or to a composition (e.g., an aqueous composition) comprising the particles. In these embodiments, the surfactant can facilitate the water-dispersibility of less-hydrophilic particles.

The particles are configured to receive and retain a first biological derivative as described herein. "Configured to receive and retain" a biological derivative, as described herein, means that the biological derivative preferentially partitions from an aqueous liquid or hydrogel onto to (e.g., onto and/or into) the polymeric particles. The partitioning thereby decreases the concentration of first biological derivative in the bulk aqueous liquid or hydrogel and correspondingly increases the amount of first biological derivative retained by the particles. In the embodiments wherein the particles comprise a surfactant and/or a surfactant is added to a composition comprising the particles, the surfactant may facilitate the receiving and/or the retention of the first biological derivative by a particle. Without being bound by theory, the accumulation of the biological derivative onto and/or into the substrate material may occur through one or more of a variety of chemical attractive forces including, but not limited to, ionic interaction, hydrophobic interaction, van der Waal's forces, and hydrogen bonding, for example.

Nonlimiting examples of suitable particles include particles comprising acrylate polymers, polystyrene polymers, cellulosic polymers, dextran polymers, and combinations or derivatives of any of the foregoing. Commercially-available particles are suitable for use in the inventive methods. These particles include, for example, Soken MX, MR and MP series, Soken SGP series, and Soken SX-500 series (all available from Soken Chemical and Engineering, Osaka, Japan); Eudragit™ RLPO and S-100 series (available from Evonik Industries, Newark, Del.); Amberlite™ nonionic absorbers and Amberlite™ ion exchange resins (available from Sigma Chemical Co., St. Louis, Mo.); Amberlyst™ ion exchanges resins (available from Alfa Aesar, Ward Hill, Mass.); Whatman QA 52 and Whatman DE 53 (available from GE Healthcare (Piscataway, N.J.); and Sephadex™ particles (available from Sigma Chemical Co.

A variety of particle sizes are suitable for use according to the present disclosure. In some embodiments, the particles can have a mean particle diameter of about 0.4 microns, about 1.0 microns, about 1.8 microns, about 2.0 microns, about 5.0 microns, about 10.0 microns, or about 20.0 microns. In some embodiments, the particles preferably can be between about 0.01 microns and about 1 millimeter, more preferably between about 0.05 microns and about 20 microns, even more preferably between about 0.1 microns and about 5 microns, even more preferably between about 0.2 microns and about 2 microns.

Methods according to the present disclosure include forming an aqueous dispersion comprising the first indicator reagent and the plurality of particles that receive and retain a first biological derivative. In some embodiments, the particles and/or the first indicator reagent can be provided in a substantially dry form and can be mixed with an aqueous liquid (e.g., water, an aqueous buffer, a nutrient broth, an aqueous sample) or hydrogel, either separately or simultaneously, wherein the particles are substantially dispersed in the aqueous liquid. In certain preferred embodiments, the particles are substantially uniformly dispersed in the aqueous liquid or hydrogel. In some embodiments, a surfactant can be added to the aqueous mixture to facilitate the water-dispersibility of the particles. Typically, forming an aqueous dispersion comprises mixing the aqueous liquid and the particles (e.g., mixing by agitation, stirring, and the like).

In some embodiments of the method, the aqueous liquid can further comprise a gelling agent. In some embodiments, the gelling agent can comprise agar. In some embodiments, the gelling agent can comprise a cold water-soluble gelling agent.

Suitable cold-water-soluble gelling agents include both natural and synthetic gelling agents that form solutions or hydrogels in water at room temperature. Nonlimiting examples of suitable gelling agents include hydroxyethyl cellulose, carboxymethyl cellulose, poly-acrylamide, locust bean gum, guar gum, xanthan gum and algin, as well as super-absorbent materials, including glycol modified polysaccharides, and starch-graft-poly(sodium acrylate-co-acrylamides), such as WATER LOCK super absorbent agents (SNI Solutions, Geneseo, Ill.). In a preferred embodiment, guar gum and xanthan gum are combined in a 1:2 weight ratio. In these embodiments, forming an aqueous mixture comprising the first indicator reagent and the plurality of particles can comprise forming a hydrogel in which the first indicator reagent is dissolved and/or suspended and in which the particles are dispersed (e.g., suspended). In some embodiments, the hydrogel composition may further comprise a surfactant.

Methods according to the present disclosure include bringing a sample that may comprise a first microorganism into fluid communication with the aqueous dispersion comprising the first indicator reagent and the plurality of particles described herein. In some embodiments, bringing the sample into fluid communication with the aqueous dispersion comprises mixing the sample with the aqueous dispersion. For example, if the sample comprises a liquid, the sample can be combined with the aqueous dispersion in a vessel (e.g., a flask, a beaker, a tube, a microwell). For example, if the sample is a solid, the sample can be suspended, and optionally homogenized, in a liquid and, subsequently, the suspension or homogenate can be combined with the aqueous dispersion. Alternatively, a solid sample may be directly suspended, and optionally homogenized, in the aqueous dispersion comprising the first indicator reagent and the plurality of particles. In some embodiments, the sample may be captured and retained on a porous membrane (e.g., a filter membrane) and the membrane can be contacted with the aqueous dispersion wherein the sample remains on one side of the membrane and the aqueous dispersion remains on the opposite side of the membrane, wherein the aqueous liquid can pass through the membrane and, thus, the sample and the aqueous dispersion are in fluid communication.

Bringing the sample into fluid communication with the aqueous dispersion permits a biological activity associated with the first microorganism, if present, to interact with the first biological indicator to form the first biological derivative. Simultaneously and/or subsequently, the first biological derivative associates with at least one of the plurality of particles.

In any of the embodiments of the method, bringing the sample into fluid communication with the aqueous dispersion can further comprise incubating the sample and the aqueous dispersion, while they are in fluid communication, for a period of time. "Incubating", as used herein means providing conditions that facilitate one or more biological activity associated with the first microorganism. A person having ordinary skill in the art will recognize conditions that facilitate biological activities associated with microorganism (e.g., a target microorganism). Nonlimiting examples of such conditions include temperature; the presence or amount of gases such as oxygen and/or carbon dioxide; the presence or amount of nutrients, vitamins, and/or cofactors; pH; oxidation-reduction potential; and incubation period. In general, longer incubation periods permit the production of greater amounts of first biological derivative by the biological activity.

Methods according to the present disclosure include detecting a presence or absence of the first biological derivative, wherein the first biological derivative is retained by one or more of the plurality of particles. In some embodiments, the first biological derivative can comprise a chromophore and, thus, can be detected by detecting a color (e.g., a color characteristic of the chromophore) retained by one or more of the particles. The color can be detected by any means of detecting a colored particle known in the art (e.g., by absorbance, reflectance). In some embodiments, the first biological derivative can comprise a fluorophore and, thus, can be detected by detecting fluorescence retained by one or more of the particles. The fluorescence can be detected by any means of detecting fluorescent particles known in the art.

In some embodiments, detecting the presence or absence of a biological derivative retained by one or more particles can comprise using an instrument or combinations of instruments (e.g., a microscope, a camera) to detect the biological derivative retained by one or more particles. In some embodiments, detecting the presence or absence of a biological derivative retained by one or more particles can comprise detecting the biological derivative retained by a plurality of particles visually.

Figure 2:
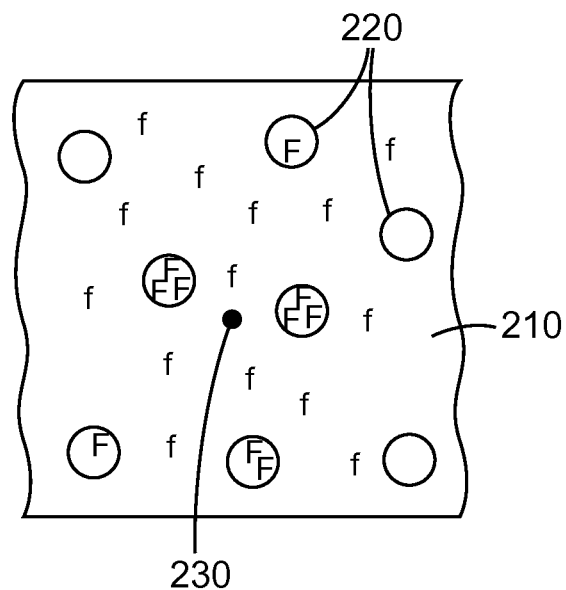
FIG. 2 is a cross-sectional side view of one embodiment of an aqueous liquid comprising a plurality of particles, according to the present disclosure.

An illustration will help demonstrate certain aspects of the present disclosure. FIG. 2 shows cross-sectional view of an aqueous liquid 210 including a plurality of particles 220 dispersed therein. The particles 210 can be any suitable particle that receives and retains a first biological derivative, as described herein. The aqueous liquid 210 can be a liquid in a suitable vessel liquids (not shown; e.g., a tube, a flask, a beaker, a petri dish, a microwell, or the like) for holding liquids. The aqueous liquid 210 comprises a first indicator reagent (not shown) dissolved and/or suspended in the liquid. In some embodiments, the aqueous liquid 210 can comprise a nutrient to support the growth of a microorganism. Also shown in FIG. 2 is a biological agent 230. The biological agent 230 is a source (e.g., a cell, a tissue, a colony, a mycelium, etc.) of biological activity (e.g., an enzyme activity).

As the biological agent 230 reacts with the first indicator reagent, it produces a free first biological derivative ("f"). The free first biological derivative "f" can be slightly- to extremely-water-soluble and, thus, can diffuse away from the biological agent 230 through the aqueous liquid 210. As the free first biological derivative "f" contacts a particle 220, the free first biological derivative "f" is received and retained by the particle 220, wherein it becomes a retained first biological derivative ("F"). As can be seen in FIG. 2, the local concentration of the retained first biological derivative "F" can be higher in the particles 220 than in the surrounding aqueous medium 210. Advantageously, this higher local concentration of the retained first biological derivative "F" can make the first biological derivative more easily detectable then the free first biological derivative "f". In some embodiments, the conversion of the free first biological derivative "f" to the retained first biological derivative "F" can further enhance the detection of the first biological derivative. For example, in some embodiments, the interaction of a weakly fluorescent free first biological derivative "f" and the particle can potentiate the fluorescence of the retained first biological derivative "F" by, for example, decreasing a fluorescence quenching effect of the aqueous liquid. For example, in some embodiments, the interaction of a first-colored free first biological derivative "f" and the particle can result in a change of the color and/or intensity of color of the retained first biological derivative "F".

It will be recognized that the advantages described in the illustrated embodiment can also be realized in an aqueous liquid 210 that comprises a hydrogel (not shown). For example, the hydrogel could be a hydrogel in a culture device (e.g., a petri dish, a thin film culture device such as, for example a PETRIFILM culture device). Furthermore, additional advantages may be obtained in a composition comprising a hydrogel. Specifically, the hydrogel can restrict the movement of particles 220 suspended therein or disposed thereon. Thus, as the free first biological derivative "f" is received and retained (thereby becoming the retained first biological derivative "F"), it is no longer capable of freely diffusing in the hydrogel.

Typically, when a biological agent releases freely-diffusible products into a hydrogel, over time, the products can diffuse away from the biological agent and accumulate in the form of very large zones surrounding the biological agent. This phenomenon is described, for example, in U.S. Pat. No. 5,601,998; which is incorporated herein by reference in its entirety. Advantageously, the methods and composition of the present disclosure provide a means to restrict the diffusion of water-soluble biological derivatives. This can be particularly advantageous when attempting to enumerate a plurality of sources of biological activity (e.g., colony-forming units), which may be in relatively close proximity, on or in a hydrogel.

Figure 3:
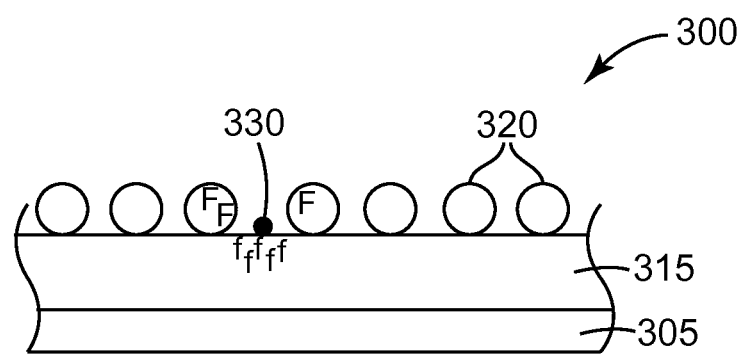
FIG. 3 is a cross section side view of one embodiment of an article comprising a hydrogel with a plurality of particles disposed thereon, according to the present disclosure

FIG. 3 shows a cross-sectional side view of a diagnostic device 300 according to the present disclosure. The diagnostic device 300 comprises a waterproof substrate 305. The waterproof substrate 305 can be, for example a petri dish, or a thin film culture device such as, for example the thin film culture devices described in U.S. Pat. Nos. 4,565,783; 5,089,413; 5,232,838; 5,601,998; 5,681,712; 7,141,387; and in U.S. Patent Application No. 61/360,166; each of which is incorporated herein by reference in its entirety. The device 300 further comprises a hydrogel 315. The hydrogel 315 comprises a first indicator reagent (not shown). The first indicator reagent can be any suitable first indicator reagent as described herein. In some embodiments, the hydrogel 315 can comprise a nutrient to support the growth of a microorganism.

Disposed on a major surface of the hydrogel 315 is a plurality of particles 320. The particles 320 can be any suitable particle that receives and retains a first biological derivative, as described herein. Also shown in FIG. 3 is a biological agent 330 (e.g., a source of biological activity, as described above). The biological agent 330 can be disposed on a major surface of the hydrogel 315 (e.g., as in microbiological surface-plating techniques), as shown in FIG. 3, or can be suspended in the hydrogel (e.g., as in microbiological pour-plating techniques), as shown in FIG. 2 and described above.

Referring back to FIG. 3, the biological agent 330, reacts with the first indicator reagent, it produces a free first biological derivative ("f"), as described above. The free first biological derivative diffuses through the aqueous liquid (e.g., hydrogel 315) surrounding the biological agent 330, as described above. Upon contact with one of the plurality of particles 320, the free first biological derivative "f" is received and retained by the particle 320 and become the retained first biological derivative ("F"), as described above.

In the embodiment shown in FIG. 3, the biological agent 330 (which may originally be part of a sample to be tested), the plurality of particles 320, and the first indicator reagent (not shown), can be brought into fluid contact with the hydrogel 315 either separately or in any combination. In some embodiments, the hydrogel 315 can be formed using an aqueous liquid comprising the first indicator reagent and/or a sample comprising the biological agent 330. In some embodiments, the biological agent 330 can be in fluid contact with a hydrogel 315 comprising the first indicator reagent for a period of time before the plurality of particles 320 are brought into fluid contact with the hydrogel 315.

In any of the embodiments, the method further can comprise providing a second indicator reagent that can be converted by a second biological activity to a second biological derivative. In these embodiments, forming the aqueous dispersion comprising the first indicator reagent and the plurality of particles comprises forming an aqueous dispersion including the second indicator reagent. In these embodiments, the method further comprises detecting a presence or absence of the second biological derivative.

In some embodiments, the presence of the second biological derivative is indicative of the presence of the first microorganism. Thus, in these embodiments, it may be possible to detect the presence of the first biological derivative and the presence of the second biological derivative associated with the presence of a first microorganism in the sample. Advantageously, in these embodiments, the second biological indicator can function to independently confirm a result obtained using the first indicator reagent. In some embodiments, the second indicator reagent can comprise a fluorophore. In some embodiments, the fluorescent second biological derivative thereof can react with a fluorescent first biological derivative in a fluorescence resonance energy transfer (FRET) reaction. FRET reactions are known in the art and, according to the present disclosure, can be indicative of the presence of both a first and second biological activity.

In some embodiments, the presence of the second biological indicator is indicative of the presence of a second microorganism. Thus, in these embodiments, it may be possible to detect the presence of a first microorganism by detecting the presence of the first biological derivative and to detect the presence of a second microorganism by detecting the presence of the second biological derivative. Advantageously, in these embodiments, the second biological indicator can function to indicator the presence of more than one microorganism in the sample.

The second indicator reagent can be any chromogenic or fluorogenic indicator reagent, as described herein, that can be reacted with a biological activity to form a second biological derivative, wherein the second biological derivative is separately-detectable (i.e., distinguishable) from the first biological derivative and, wherein neither the second biological indicator nor the second biological derivative substantially interferes with the conversion of the first indicator to the first biological derivative nor substantially interferes with the detection of the first biological derivative retained by at least one of a plurality of particles.

In any of the embodiments, the method further can comprise separating at least a portion of the plurality of particles from the aqueous dispersion. Typically, the separating takes place after the sample has been brought into contact with the aqueous dispersion comprising the first indicator reagent and the plurality of particles. In some embodiments, separating at least a portion of the plurality of particles can comprise separating one or more particles from at least a portion of the aqueous liquid. In some embodiments, separating at least a portion of the plurality of particles from at least a portion of the aqueous liquid is a process to form a local concentration of the separated particles in the original volume of the aqueous liquid (e.g., by sedimentation, flocculation, or centrifugation). Additionally or alternatively, in some embodiments, separating at least a portion of the plurality of particles from at least a portion of the aqueous liquid is a process to concentrate the separated particles in a smaller volume of the aqueous liquid or to substantially remove the aqueous liquid from the portion (e.g., by removing at least a portion of the aqueous liquid by decanting, pipetting or by filtration). In some embodiments, the separating step can be used to localize one or more of the particles in an optical path in a detection instrument (e.g., a fluorescent cell sorter).

As described above, the methods of the present disclosure can comprise forming an aqueous dispersion comprising the first indicator reagent, the plurality of particles that receive and retain the first biological derivative, and a gelling agent. In some embodiments, the aqueous dispersion comprising the gelling agent can further comprise the sample (e.g., as in an agar pour plate technique or in certain common techniques using PETRIFILM culture media available from 3M Company (St. Paul, Minn.), the sample is distributed in the gel that is formed).

In some alternative embodiments, an aqueous dispersion comprising the plurality of particles the gelling agent and, optionally, the first indicator reagent can be formed. After the gel is formed, the sample and, if not already present in the aqueous dispersion, the first indicator reagent can be distributed onto at last a portion of a surface of the gel (e.g., as in common surface plating techniques used with agar media). Optionally, the composition that includes the sample can be incubated for a period of time, as described herein. The particles are observed to detect a presence or absence of the first biological derivative, wherein the first biological derivative is retained by a particle. In any of these embodiments, a second indicator reagent as described herein can be brought into fluid contact with the aqueous dispersion (e.g., by adding the second indicator reagent to the aqueous dispersion prior to formation of the gel or by distributing the second indicator reagent onto the surface of the gel after the gel is formed).

In some alternative embodiments, an aqueous gel (e.g., an aqueous gel comprising agar or other suitable gelling agents known in the art or described herein) can be formed. Optionally, the aqueous gel can comprise the first indicator reagent. After the gel is formed, the sample, plurality of particles and, if not already present in the aqueous gel, the first indicator reagent can be distributed onto at least a portion of a surface of the gel. Optionally, the composition that includes the sample can be incubated for a period of time, as described herein. The particles are observed to detect a presence or absence of the first biological derivative, wherein the first biological derivative is retained by a particle. In any of these embodiments, a second indicator reagent as described herein can be brought into fluid contact with the aqueous dispersion (e.g., by adding the second indicator reagent to the aqueous dispersion prior to formation of the gel or by distributing the second indicator reagent onto the surface of the gel after the gel is formed).

The present disclosure provides a composition. In some embodiments, the composition can be used in methods to detect the presence of a first microorganism, as described herein. The composition comprises water, a first indicator reagent that can be converted by a first biological activity to a first biological derivative, and a plurality of particles. The particles can receive and retain the first biological derivative from an aqueous liquid, as described herein. In some embodiments, the composition can further comprise a nutrient. The nutrient can facilitate the growth and/or metabolism of a microorganism (e.g., a first microorganism and/or a second microorganism, as described herein). In any of the embodiments, the composition can further comprise a gelling agent. In some embodiments, the gelling agent can comprise a cold-water-soluble gelling agent. In some embodiments, the gelling agent can be selected from the group consisting of hydroxyethyl cellulose, carboxymethyl cellulose, poly-acrylamide, locust bean gum, guar gum, xanthan gum and algin, as well as super-absorbent materials, including glycol modified polysaccharides, and starch-graft-poly(sodium acrylate-co-acrylamides). The gelling agent can react with the water to form a hydrogel. In any of the embodiments of the composition, at least a portion of the plurality of particles can be dispersed (e.g., suspended) in the hydrogel. In any of the embodiments of the composition, at least a portion of the plurality of particles can be disposed on a major surface of the hydrogel. In any of the embodiments, the composition can further comprise a surfactant. Advantageously, the surfactant can facilitate the water-dispersibility of the particles in the composition. The surfactant can be an anionic surfactant, a nonionic surfactant, or a cationic surfactant. The surfactant can be selected from the group consisting of sulfates, sodium dodecyl sulfate, sulfonates, sodium dodecylbenzene sulfonate, long chain carboxylates, phosphate esters, quaternary ammonium salts, dodecyltrimethylammonium chloride, polysorbates, Tween™ surfactants (e.g., Tween 20™), Span™ surfactants, alcohol ethoxylates, Triton X-100, polyethylene oxide derivatives, and copolymers comprising polypropylene oxide (e.g.: Pluronic™ or Tergitol™ surfactants).

In any of the embodiments, the composition can further comprise a second indicator reagent that can be converted by a biological activity to a second biological derivative. The second indicator reagent can be any chromogenic or fluorogenic indicator reagent, as described herein, that can be reacted with a biological activity to form a second biological derivative, wherein the second biological derivative is separately-detectable (i.e., distinguishable) from the first biological derivative and, wherein neither the second biological indicator nor the second biological derivative substantially interferes with the conversion of the first indicator to the first biological derivative nor substantially interferes with the detection of the first biological derivative retained by at least one of a plurality of particles.

In another aspect, the present disclosure provides an article. The article can be used to detect a first microorganism (e.g., a target microorganism in a diagnostic test). In some embodiments, the article can be an article comprising dry culture medium such as, for example, the culture devices described in U.S. Pat. Nos. 4,565,783; 5,089,413; 5,232,838; 5,601,998; 5,681,712; 7,141,387; and in U.S. Patent Application No. 61/360,166.

The article can comprise a body member comprising a self-supporting, waterproof substrate having a first major surface and a second major surface and a coating adhered to a least a portion of the first major surface. The coating comprises a gelling agent and a plurality of particles. The particles receive and retain from a hydrogel a first biological derivative of a first indicator reagent and can comprise any suitable particle as described herein. In some embodiments, the particles comprise an organic polymer selected from the group consisting of acrylate polymers, polystyrene polymers, cellulosic polymers, dextran polymers, and combinations or derivatives of any of the foregoing. Commercially-available particles are suitable for use in the inventive methods. These particles include, for example, Soken MX, MR and MP series, Soken SGP series, and Soken SX-500 series (all available from Soken Chemical and Engineering, Osaka, Japan); Eudragit™ RLPO and S-100 series (available from Evonik Industries, Newark, Del.); Amberlite™ nonionic absorbers and Amberlite™ ion exchange resins (available from Sigma Chemical Co., St. Louis, Mo.); Amberlyst™ ion exchanges resins (available from Alfa Aesar, Ward Hill, Mass.); Whatman QA 52 and Whatman DE 53 (available from GE Healthcare (Piscataway, N.J.); and Sephadex™ particles (available from Sigma Chemical Co. In some embodiments, the particles are monodisperse particles. In some embodiments, the average particle diameter preferably is between about 0.01 microns and about 1 millimeter, more preferably between about 0.05 microns and about 20 microns, even more preferably between about 0.1 microns and about 5 microns, even more preferably between about 0.2 microns and about 2 microns. In some embodiments, the coating can comprise a dehydrated cold-water-reconstitutable coating that comprises the gelling agent with the plurality of particles dispersed therein and can be prepared as described, for example, in U.S. Pat. No. 4,565,783, and in the Examples herein.

In any embodiment, the article can further comprise an adhesive layer disposed between and adhesively coupled to the first major surface of the base layer and the coating. In some embodiments, the coating comprises a dry powder coating comprising the gelling agent and the plurality of particles and can be prepared as described, for example, in U.S. Pat. No. 4,565,783.

In any embodiment of the article, the coating and/or adhesive layer can further comprise the first indicator reagent. The first indicator reagent can be any suitable first indicator reagent as described herein. In any embodiment of the article, the coating or the adhesive layer can comprise a second indicator reagent. The second indicator reagent can be any suitable second indicator reagent as described herein. In any embodiment of the article, the coating can comprise a surfactant. The surfactant can comprise an anionic surfactant, a nonionic surfactant, or a cationic surfactant. The surfactant can be selected from the group consisting of sulfates, sodium dodecyl sulfate, sulfonates, sodium dodecylbenzene sulfonate, long chain carboxylates, phosphate esters, quaternary ammonium salts, dodecyltrimethylammonium chloride, polysorbates, Tween™ surfactants (e.g., Tween 20™), Span™ surfactants, alcohol ethoxylates, Triton X-100, polyethylene oxide derivatives, and copolymers comprising polypropylene oxide (e.g.: Pluronic™ or Tergitol™ surfactants).

Embodiments

Embodiment 1 is a method of detecting a biological activity, comprising:
  providing,
    a sample that may comprise a first biological activity;
    a first indicator reagent that can be converted by the first biological activity to a first biological derivative, wherein the first indicator reagent comprises a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores; and
    a plurality of particles, each particle comprising an organic polymer that receives and retains the first biological derivative;
  forming an aqueous dispersion comprising the first indicator reagent and the plurality of particles;
  bringing the sample into fluid communication with the aqueous dispersion; and
  detecting a presence or absence of the first biological derivative, wherein the first biological derivative is retained by a particle.

Embodiment 2 is the method of embodiment 1, wherein detecting the presence or absence of the first biological derivative comprises detecting a fluorescent first biological derivative.

Embodiment 3 is the method of embodiment 1, wherein detecting the presence or absence of the biological derivative comprises detecting a colored biological derivative.

Embodiment 4 is the method of embodiment 1 or embodiment 2, further comprising providing a gelling agent
  and wherein forming the aqueous dispersion comprises forming a hydrogel, wherein at least a portion of the plurality of particles is dispersed in the hydrogel.

Embodiment 5 is the method of embodiment 4, wherein providing a gelling agent comprising providing a cold-water-soluble gelling agent.

Embodiment 6 is the method of embodiment 5, wherein the cold water-soluble gelling agent is selected from the group consisting of hydroxyethyl cellulose, carboxymethyl cellulose, poly-acrylamide, locust bean gum, guar gum, xanthan gum and algin, glycol modified polysaccharides, and starch-graft-poly(sodium acrylate-co-acrylamides).

Embodiment 7 is the method of any one of the preceding embodiments, further comprising:
  providing a second indicator reagent that can be converted by a second biological activity to a second biological derivative; and
  detecting a presence or absence of the second biological derivative;
  wherein forming the aqueous dispersion comprises forming an aqueous dispersion comprising the second indicator reagent;
  wherein, when the second indicator reagent comprises a fluorogenic enzyme substrate, the second indicator reagent has a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores.

Embodiment 8 is the method of any one of embodiments 4 through 7, further comprising:
  providing a second indicator reagent that can be converted by a second biological activity to a second biological derivative;
  bringing the second indicator reagent into fluid communication with the hydrogel; and
  detecting a presence or absence of the second biological derivative.

Embodiment 9 is the method of any of the preceding embodiments, wherein bringing the sample into fluidic contact with the aqueous dispersion comprises forming the aqueous dispersion comprising the sample, the first indicator reagent, and the plurality of particles.

Embodiment 10 is the method of any one of the preceding embodiments wherein, after bringing the sample into fluid communication with the aqueous dispersion, the method further comprises separating a portion of the plurality of particles from or within the aqueous dispersion.

Embodiment 11 is the method of embodiment 10, wherein separating the portion comprises separating the portion by sedimentation, centrifugation, flocculation, or filtration.

Embodiment 12 is a method of detecting a biological activity, comprising:
providing,
  a sample that may comprise a first biological activity;
  a first indicator reagent that can be converted by the biological activity to a first biological derivative, wherein the first indicator reagent comprises a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores;
  a plurality of particles, each particle comprising an organic polymer that receives and retains the first biological derivative; and
  a gelling agent;
forming a hydrogel comprising the first indicator reagent and the gelling agent;
distributing the particles on at least a portion of a major surface of the hydrogel;
bringing the sample into fluid communication with a portion of the hydrogel; and
detecting a presence or absence of the first biological derivative, wherein the first biological derivative is retained by a particle, wherein the presence of the first biological derivative is indicative of the presence of a first biological activity.

Embodiment 13 is the method of embodiment 12, wherein detecting the presence or absence of the first biological derivative comprises detecting a fluorescent first biological derivative or a colored first biological derivative.

Embodiment 14 is the method of embodiment 12 or embodiment 13, wherein providing the gelling agent comprises providing a cold water-soluble gelling agent.

Embodiment 15 is the method of embodiment 14, wherein the cold-water-soluble gelling agent is selected from the group consisting of hydroxyethyl cellulose, carboxymethyl cellulose, poly-acrylamide, locust bean gum, guar gum, xanthan gum and algin, glycol modified polysaccharides, and starch-graft-poly(sodium acrylate-co-acrylamides).

Embodiment 16 is the method of any one of the embodiments 12 through 15, further comprising:
providing a second indicator reagent that can be converted by a second biological activity to a second biological derivative;
binging the second indicator into fluid communication with the hydrogel; and
detecting a presence or absence of the second biological derivative;
wherein the presence of the second biological derivative is indicative of the presence of the first biological activity.

Embodiment 17 is the method of embodiment 16, wherein distributing the particles on at least a portion of a major surface of the hydrogel further comprises bringing the second indicator reagent into fluid communication with the hydrogel.

Embodiment 18 is the method of embodiment 16, wherein bringing the sample into fluid communication with the at least a portion of a major surface of the hydrogel further comprises bringing the second indicator reagent into fluid communication with the hydrogel.

Embodiment 19 is the method of embodiment 16, wherein forming the hydrogel further comprises forming the hydrogel comprising the second indicator reagent.

Embodiment 20 is the method of any one of embodiments 12 through 15, further comprising:
providing a second indicator reagent that can be converted by a second biological activity to a second biological derivative;
bringing the second indicator into fluid communication with the hydrogel; and
detecting a presence or absence of the second biological derivative.

Embodiment 21 is the method of embodiment 20, wherein distributing the particles on at least a portion of a major surface of the hydrogel further comprises bringing the second indicator reagent into fluid communication with the hydrogel.

Embodiment 22 is the method of embodiment 20, wherein bringing the sample into fluid communication with the at least a portion of a major surface of the hydrogel further comprises bringing the second indicator reagent into fluid communication with the hydrogel.

Embodiment 23 is the method of embodiment 20, wherein forming the hydrogel further comprises forming the hydrogel comprising the second indicator reagent.

Embodiment 24 is the method of any one of embodiments 12 through 23, wherein detecting a presence or absence of the first biological derivative comprises detecting discrete fluorescent zones.

Embodiment 25 is the method of embodiment 24, wherein detecting discrete fluorescent zones further comprises counting a quantity of discrete fluorescent zones.

Embodiment 26 is the method of any one of embodiments 12 through 23, wherein detecting a presence or absence of the first biological derivative comprises detecting discrete colored zones.

Embodiment 27 is the method of embodiment 26, wherein detecting discrete fluorescent zones further comprises counting a quantity of discrete colored zones.

Embodiment 28 is a composition, comprising:
water;
a first indicator reagent that can be converted by a first biological activity to a first biological derivative; and
a plurality of particles;
wherein the first indicator reagent comprises a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores
wherein the particles are capable of receiving and retaining the first biological derivative from an aqueous liquid.

Embodiment 29 is the composition of embodiment 28, further comprising a nutrient to facilitate the growth of a microorganism.

Embodiment 30 is the composition of embodiment 28 or embodiment 29, further comprising a gelling agent.

Embodiment 31 is the composition of embodiment 30, wherein the gelling agent reacts with the water to form a hydrogel.

Embodiment 32 is the composition of embodiment 30 or embodiment 31, wherein the gelling agent comprises a cold-water-soluble gelling agent.

Embodiment 33 is the composition of embodiment 32, wherein the cold-water-soluble gelling agent is selected from the group consisting of hydroxyethyl cellulose, carboxymethyl cellulose, poly-acrylamide, locust bean gum, guar gum, xanthan gum and algin, glycol modified polysaccharides, and starch-graft-poly(sodium acrylate-co-acrylamides).

Embodiment 34 is the composition of any one of embodiments 31 through 33, wherein at least a portion of the plurality of particles is dispersed in the hydrogel.

Embodiment 35 is the composition of any one of embodiments 31 through 34, wherein at least a portion of the plurality of particles is disposed on a major surface of the hydrogel.

Embodiment 36 is the composition of any one of embodiments 28 through 35, further comprising a surfactant.

Embodiment 37 is the composition of any one of embodiments 28 through 36, wherein the particles comprise an organic polymer selected from the group consisting of acrylate polymers, polystyrene polymers, cellulosic polymers, dextran polymers, combinations of any of the foregoing and derivatives of any of the foregoing.

Embodiment 38 is an article, comprising:
a body member comprising a self-supporting, waterproof substrate having a first major surface and a second major surface; and
a coating adhered to a least a portion of the first major surface, wherein the coating comprises a gelling agent and a plurality of particles;
wherein the particles receive and retain from a hydrogel a first biological derivative of a first indicator reagent;
wherein the first indicator reagent comprises a fluorogenic enzyme substrate having a fluorophore selected from the group consisting of umbelliferone, 7-aminocoumarin, β-naphthylamine, β-naphthol, fluorescein, resorufin, 9H-(1, 3-dichloro-9,9-dimethyl acridin-2-one), rhodamine 110, a derivative of any of the foregoing fluorophores, and a combination of any of the foregoing fluorophores.

Embodiment 39 is the article of embodiment 38, wherein the gelling agent comprises a dry, cold-water-soluble gelling agent.

Embodiment 40 is the article of embodiment 39, wherein the gelling agent is selected from the group consisting of hydroxyethyl cellulose, carboxymethyl cellulose, poly-acrylamide, locust bean gum, guar gum, xanthan gum and algin, glycol modified polysaccharides, and starch-graft-poly(sodium acrylate-co-acrylamides).

Embodiment 41 is the article of any one of embodiments 38 through 40, wherein the first biological derivative is a fluorescent compound.

Embodiment 42 is the article of any one of embodiments 38 through 41, wherein the article further comprises the first indicator reagent.

Embodiment 43 is the article of any one of embodiments 38 through 42, further comprising an adhesive layer disposed between the coating and the first major surface, wherein the adhesive layer is disposed between and adhesively coupled to the first major surface and the coating.

Embodiment 44 is the article of any one of embodiments 38 through 43, wherein the coating further comprises a nutrient.

Embodiment 45 is the article of any one of embodiments 38 through 44, wherein the coating or the adhesive layer comprises a second indicator reagent.

Embodiment 46 is the article of any one of embodiments 38 through 45, wherein the coating or the adhesive layer further comprises a selective agent.

Embodiment 47 is the article of any one of embodiments 38 through 46, wherein the particles comprise an organic polymer selected from the group consisting of acrylate polymers, polystyrene polymers, cellulosic polymers, dextran polymers, combinations of any of the foregoing and derivatives of any of the foregoing.

Embodiment 48 is the article of any one of embodiments 38 through 47, wherein the coating further comprises a surfactant.

Embodiment 49 is the article of embodiment 48, wherein the surfactant comprises an anionic surfactant, a nonionic surfactant, or a cationic surfactant.

Embodiment 50 is the article of embodiment 49, wherein the surfactant is selected from the group consisting of sulfates, sodium dodecyl sulfate, sulfonates, sodium dodecylbenzene sulfonate, long chain carboxylates, phosphate esters, quaternary ammonium salts, dodecyltrimethylammonium chloride, polysorbates, Tween™ surfactants (e.g., Tween 20™), Span™ surfactants, alcohol ethoxylates, Triton X-100, polyethylene oxide derivatives, and copolymers comprising polypropylene oxide (e.g.: Pluronic™ or Tergitol™ surfactants).

Embodiment 51 is the method of any one of embodiments 1 though 27, the composition of any one of embodiments 28 through 37, or the article of any one of embodiments 38 through 50, wherein the particles are about 0.01 μm to about 1000 μm in diameter.

Embodiment 52 is the method of any one of embodiments 1 though 27 or embodiment 51, the composition of any one of embodiments 28 through 37 or embodiment 51, or the article of any one of embodiments 38 through 51, wherein the particles are water-dispersible.

Embodiment 53 is the method of any one of embodiments 1 through 27, wherein the first biological activity is an indicator of a presence of a first microorganism.

Embodiment 54 is the method of any one of embodiments 7 through 13 and embodiments 18 through 27, wherein the second indicator reagent is an indicator of a presence of the first microorganism.

Embodiment 55 is the method of any one of embodiments 7 through 13, embodiments 18 through 27, or embodiment 54, wherein the second indicator reagent is an indicator of a presence of a second microorganism.

Embodiment 56 is the method of any one of the preceding embodiments wherein the second indicator reagent, if present, comprises a chromogenic indicator reagent.

The present invention is illustrated by the following examples. It is to be understood that the particular examples, materials, amounts, and procedures are to be interpreted broadly in accordance with the scope and spirit of the invention as set forth herein.

EXAMPLES

Materials Used in the Examples
PBS—Phosphate buffered saline obtained from Sigma-Aldrich (St. Louis, Mo.)
Butterfields buffer obtained from 3M Company (St. Paul, Minn.)
Beta-D-galactosidase (Catalog #345788) obtained from EMD Biosciences (La Jolla, Calif.)
Pig liver esterase (#E3019) obtained from Sigma-Aldrich (St. Louis, Mo.)
DMSO—Dimethyl sulfoxide obtained from EMD Chemicals (Gibbstown, N.J.)
TSB—Tryptic Soy Broth—BD #211822 obtained from Becton Dickinson
Xanthan gum—KELTROL xanthan gum available from CP Kelco (Atlanta. GA)
Locust bean gum—Genu® Gum obtained from CP Kelco (Atlanta. GA)

Surfactants
- Triton X-100™—nonionic surfactant obtained from Sigma-Aldrich (St. Louis Mo.)
- Tween-20™—polysorbate surfactant obtained from Sigma-Aldrich (St. Louis, Mo.)
- SDBS—sodium dodecylbenzene sulfonate obtained from TCI America (Portland, Oreg.)
- DTAC—dodecyltrimethylammonium chloride obtained from K&K Laboratories (Plainview, N.Y.)
- SDS—sodium dodecyl sulfate obtained from Alfa Aesar (Ward Hill, Mass.)

Fluorogens:
- MHCgal—Methyl -7-hydroxycoumarin-3-carboxylate galactoside prepared as described in Chilvers et al. *J. Appl. Microbiology* 2001, 91, 1118-1130
- TUacetate—3-thienyl umbelliferone acetate prepared as described in U.S. Pat. No. 6,566,508
- TUgal—3-thienyl umbelliferone galactoside prepared as described in U.S. Pat. No. 6,566,508

Particles:
- Polyacrylate particles obtained from Soken Chemical and Engineering (Osaka, Japan):
  - MX-180—Monodisperse acrylate particles (1.8 micron mean diameter)
  - MX-2000—Monodisperse acrylate particles (20.0 micron mean diameter)
  - MX-500—Monodisperse acrylate particles (5.0 micron mean diameter)
  - MR-10HG—Polydisperse acrylate particles (10.0 micron mean diameter)
  - MR-7HG—Polydisperse acrylate particles (6.0 micron mean diameter)
  - MR-2HG—Polydisperse acrylate particles (2.0 micron mean diameter)
  - MR-2G—Polydisperse acrylate particles (1.0 micron mean diameter)
  - MP-1000—Monodisperse acrylate particles (0.40 micron mean diameter)
  - SGP-70C—Polydisperse polystyrene particles (20.0 micron mean diameter)
  - SX-500H—Monodisperse polystyrene particles (5.0 micron mean diameter)
- QA 52—Whatman QA 52—strong base anion exchange cellulose-based resin obtained from Whatman (GE Healthcare (Piscataway, N.J.)
- DE 53—Whatman DE 53—weak base anion exchange cellulose-based resin obtained from Whatman (GE Healthcare (Piscataway, N.J.)
- XAD-16—Amberlite™ XAD-16—nonionic polystyrene-based absorbent obtained from Sigma-Aldrich
- G-75-50—Sephadex™ G-75-40 cross linked dextran obtained from Sigma-Aldrich
- S-300—Sephacryl™ S-300 allyl dextran particles obtained from GE Healthcare
- IR-45CP—Amberlite™ IR-45CP—weakly basic macroreticular polystyrene anion exchange resin was obtained from Mallinckrodt (Paris, Ky.)
- IRA-400CP—Amberlite™ IRA-400CP—strongly basic polystyrene anion exchange resin obtained from Mallinckrodt (Paris, Ky.)
- A-21—Amberlyst™ A-21—weakly basic macroreticular polystyrene anion exchange resin was obtained from Alfa Aesar (Ward Hill, Mass.)
- MAPTAC—[3-(methacryloylamino)propyl]trimethylammonium chloride dispersion, about 10% by weight in water, prepared according to U.S. Pat. No. 7,647,835

Preparation of a Culture Plate

A mixture of 50 g of xanthan gum powder and 50 g of locust bean gum powder was placed in a 500 mL bottle and shaken manually for about 5 minutes. A cover film was prepared by sprinkling the mixture onto the adhesive side of a pressure-sensitive adhesive coated sheet (9795R Advanced Sealing Tape obtained from 3M Company (St. Paul, Minn.). The coating weight of the gums was approximately 85 mg/24 square inches.

A nutrient mixture was prepared by mixing 22.8 parts of pancreatic digest of casein, 15.9 parts of yeast extract, 45.5 parts of sodium pyruvate, 4.1 parts of dextrose, 9.0 parts of potassium phosphate, dibasic, and 2.8 grams of potassium phosphate, monobasic. A nutrient broth was prepared by mixing 500 mL of deionized water with 14.78 grams of the above nutrient mixture in a beaker using an air motor mixer. Then 5 grams of locust bean gum were mixed with the broth in small increments followed by mixing thoroughly for several minutes. The beaker was then covered with foil and the mixture was heated to 80° C. and mixed for about 6 minutes and then allowed to cool for about ten minutes while mixing without heat. The broth was then poured into a sterilized beaker, covered with a plastic bag and refrigerated. The cooled broth was stirred carefully with a spatula to avoid forming air bubbles and then knife coated onto a 9.5 inch wide, 4 mil thick sheet of polyethylene terephthalate film (available as MELINEX 453 from DuPont Teijin Films, (Hopewell, Va.) to a dry coating weight of about 150 mg per 24 square inches (about 1 mg per square centimeter). The coated film was dried in an oven set at a temperature of 210° C. for about 10 minutes.

A laminate was prepared by laminating an 8 inch (20.3 cm) wide sheet of 4 mil thick polystyrene foam to a pressure-sensitive adhesive transfer tape on a liner. Circular discs measuring 5 cm in diameter were die-cut from the laminate to form a circular cut-out disc centered within a 3 inch (7.6 centimeter) square on the laminate, and the discs were removed. The liner was removed from the remaining laminate and the adhesive-coated surface of the polystyrene foam was adhered to the broth coated sheet, to provide a base member having a broth-coated self-supporting substrate and a hydrophobic spacer element (i.e., "foam dam") adhered to the broth-coated surface of the supporting substrate. Rectangular plates measuring 3 inches by 4 inches (7.6 centimeter by 10.16 centimeter) were cut from the laminate, with the circular cut-out opening centered within a 3 inch (7.6 centimeter) square from one end of the 4 inch length. The cover film was placed over the plate with the powder coated side facing the foam dam and attached with a double sided pressure-sensitive adhesive tape to form a culture plate.

Examples 1-7 & C1

TUacetate with particles and enzyme

A dye solution was prepared by dissolving a 1 mg of TUacetate in 1 mL DMSO. An aqueous particulate dispersion was prepared by mixing 0.5 mL of the dye solution with approximately 100 mg of the particles shown in Table 1 in a vial. Then 50 µL of pig liver esterase (1 mg/mL in PBS) was added to each vial to liberate fluorescent TU. The vials were observed for fluorescence under a standard laboratory fluorescent lamp (365 nm). The fluorescence was ranked as follows: --- or none; +(weak); ++ (moderately weak); +++ (moderate); ++++ (strong). Observations are shown in Table 1 for each particle and without particles.

TABLE 1

Fluorescence of TUacetate with particles

| Ex | Particle | Fluorescence in particles (color) |
|---|---|---|
| 1 | IR-45 | + |
| 2 | IRA-400 CP | +++ (Green) |
| 3 | A-21 | +++ (Green) |
| 4 | XAD-16 | ++ (Blue) |
| 5 | G-75-40 | +++ (blue-green) |
| 6 | QA 52 | +++ (green) |
| 7 | DE53 | +++ (blue) |
| C1 | None | Bright blue-green fluorescence in solution |

Spectroscopic measurements (not shown) were made on the solutions using a SpectraMax M5 fluorescence plate reader from Molecular Devices. The results indicate that in ionic matrices (e.g., QA52, IRA-400CP) the fluorophore emits from the ionic state. In non-ionic matrices, or those containing active protons (weak base), e.g., DE-53, emissions from the neutral state can dominate.

Examples 8-10 and C2

Comparisons with and without Enzyme Solution

Dye solutions were prepared by dissolving 1 mg of either TUgal or MHCgal in 1 ml of DMSO. An enzyme reagent solution was prepared by mixing about 200 µL of beta-galactosidase stock solution with 0.7 mL of beta-mercaptoethanol, 0.2 g of $MgCl_2$ and diluting to 10 mL with deionized water. Aliquots of 10 µL portions of the dye solution were added to vials, each containing 1 mL of PBS, 50 µL of reagent solution and 100 mg of one of the particles shown in Table 2. Control samples were prepared without the reagent (enzyme) solution. The vials were inspected after 0.5 hour and ranked as described in Example 1.

TABLE 2

Fluorescence with and without enzyme

| | | Fluorescence | | | |
|---|---|---|---|---|---|
| Ex | Particle | MHCgal w/o enzyme | MHCgal w enzyme | TUgal w/o enzyme | TUgal w/ enzyme |
| 8 | IRA 400-CP | + | +++ | n/a | + |
| 9 | IRA 410 | None | + | n/a | +++ (green) |
| 10 | QA-52 | None | +++ | + (blue) | +++ (green) |
| C2 | None (solution) | None | +++ | Blue | Green | n/a—data not available

In Examples 8-10, the fluorescence seen came from the particles, not the solution. This indicates that the fluorescent signal of soluble fluorophores may be sequestered into a solid phase by using the appropriate particles.

Examples 11-16, C3

Fluorescence of E. Coli in Plates with Particles and MHCgal

A dye solution was prepared by adding MHCgal to DMSO to make a 20 mM solution. Aqueous particulate dispersions for Examples 11-14 were prepared by adding 250 mg of one of the particles shown in Table 3 to 5 mL of Butterfield's Buffer, and sonicating in an ultrasonic bath for 50 minutes at room temperature.

Aqueous particulate dispersions for Examples 15 and 16 were prepared by diluting 1 mL of Sephacryl S-300 or MAPTAC four-fold with Butterfield's Buffer.

An overnight culture of E. coli (ATCC #11229) was prepared by inoculating a single colony into 10 mL of TSB (Tryptic Soy Broth). The culture was shaken at 30° C. and 200 rpm in an Innova 4000 incubator shaker (New Brunswick Scientific) for 24 hours. The next morning, the overnight culture was diluted 100-fold three times with Butterfields buffer to provide a solution containing an estimated $10^3$ organisms/mL solution.

A 1 mL aliquot of each one of the particulate dispersions was mixed with 8 µL of the MHCgal dye solution and 10 µL of the diluted E. coli culture. Each of the dispersions was inoculated into a separate culture plate prepared as described above. The culture plates were incubated at 30° C. for 18 hours, then inspected for fluorescence and ranked. Results are shown in Table 3.

TABLE 3

Fluorescence of E. coli plates with particles and a fluorogenic dye

| Example | Particle | Fluorescence |
|---|---|---|
| 11 | MX-180 | +++ |
| 12 | MR-2G | ++ |
| 13 | MP-1000 | --- |
| 14 | DE-53 | --- |
| 15 | S-300 | --- |
| 16 | MAPTAC | + |
| C3 | None | + |

The data in these examples show the enhanced detection of microorganisms in a rehydrated media by using a non-precipitating fluorophore and solid particles.

Examples 17-21 and C4

Effect of Surfactants

Dye solutions were prepared by adding TUgal to DMSO to make a 20 mM solution. This was further diluted with DMSO to make a 1 mM solution. A reagent solution was prepared by mixing about 200 µL of beta-galactosidase stock solution with 0.7 mL of beta-mercaptoethanol, 0.2 g of $MgCl_2$ and diluting to 10 mL with deionized water. An aqueous dispersion was prepared by adding 10 µL of the 1 mM dye solution to 2 mL of PBS containing 50 µL of reagent solution and 60 mg of the particle shown in Table 8 for Examples 17-20. Example 21 was prepared without particles. Examples 17-21 also included 0.5 mg/mL of the surfactant listed in Table 8. Example C4 was prepared without particles and without the enzyme solution.

TABLE 8

Effect of surfactants and particles with TUgal

| | | | Surfactant | | | |
|---|---|---|---|---|---|---|
| Ex | Particles | Fluorophore | None | DTAC | Triton X-100 | SDBS |
| 17 | SX-350H | TUgal | Green | Dark green | Blue | Blue |
| 18 | QA 52 | TUgal | Green | Green | Green | Blue |
| 19 | IR-45CP | TUgal | Green | Green | Green | Green |

TABLE 8-continued

Effect of surfactants and particles with TUgal

| | | | Surfactant | | | |
|---|---|---|---|---|---|---|
| Ex | Particles | Fluoro-phore | None | DTAC | Triton X-100 | SDBS |
| 20 | XAD-16 | TUgal | Blue | Blue/Green | Blue | Blue |
| 21 | None | TUgal | Blue/green | Dark green | Blue/green | Blue/green |
| C4 | None | TUgal | Blue | NT | NT | NT |

NT—Not Tested

The data in Table 8 shows the change in fluorescent emission of TUgal with surfactants.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications, publications, and nucleic acid and protein database entries which are cited herein, are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of detecting a biological activity, comprising:
providing,
a sample that may comprise a first biological activity;
a first indicator reagent that can be converted by the biological activity to a first biological derivative, wherein the first indicator reagent comprises a fluorogenic enzyme substrate having a fluorophore selected from the group consisting of umbelliferone, 7-aminocoumarin, β-naphthylamine, β-naphthol, fluorescein, resorufin, 9H-(1,3-dichloro-9,9-dimethyl acridin-2-one), rhodamine 110, a derivative of any of the foregoing fluorophores, and a combination of any of the foregoing fluorophores;
a plurality of particles, each particle comprising an organic polymer that receives and retains the first biological derivative, wherein the organic polymer is selected from the group consisting of acrylate polymers, polystyrene polymers, cellulosic polymers, dextran polymers, a combination of any of the foregoing and a derivative of any of the foregoing; and
a gelling agent;
forming a hydrogel comprising the first indicator reagent and the gelling agent;
distributing the particles on at least a portion of a major surface of the hydrogel;
bringing the sample into fluid communication with a portion of the hydrogel, wherein the first biological derivative partitions from hydrogel onto and/or into the plurality of particles; and
detecting a presence or absence of the first biological derivative, wherein the first biological derivative is retained by a particle, wherein the presence of the first biological derivative is indicative of the presence of a first biological activity, wherein detecting the presence of the first biological derivative comprises counting a quantity of discrete fluorescent zones, and
wherein the particles are between about 0.05 microns and about 20 microns.

2. The method of claim 1, further comprising:
providing a second indicator reagent that can be converted by a second biological activity to a second biological derivative;
bringing the second indicator into fluid communication with the hydrogel; and
detecting a presence or absence of the second biological derivative;
wherein the presence of the second biological derivative is indicative of the presence of the first biological activity.

3. The method of claim 1, further comprising:
providing a second indicator reagent that can be converted by a second biological activity to a second biological derivative;
bringing the second indicator into fluid communication with the hydrogel; and
detecting a presence or absence of the second biological derivative.

* * * * *